United States Patent [19]
Kiyomine et al.

[11] Patent Number: 5,720,944
[45] Date of Patent: Feb. 24, 1998

[54] COMPOSITION FOR PERMANENT WAVING OF HUMAN HAIR

[75] Inventors: Akira Kiyomine, Kawachi-gun; Yukihiro Kondo, Utsunomiya, both of Japan; Kenichi Morita, Bensheim, Germany; Shinobu Nagase, Haga-gun, Japan; Koichi Nakamura; Yoshinori Nishizawa, both of Utsunomiya, Japan; Bernd Nöcker, Ober-Ramstadt, Germany; Hitoshi Sakaguchi, Haga-gun; Hiroyuki Suzuki, Kawachi-gun, both of Japan

[73] Assignee: Kao Corporation, Japan

[21] Appl. No.: 619,435

[22] Filed: Mar. 21, 1996

[30] Foreign Application Priority Data

Mar. 30, 1995 [JP] Japan .......................... 7-072698
May 29, 1995 [DE] Germany .............. 195 19 581.7

[51] Int. Cl.$^6$ ........................... A61K 7/09; A61K 7/06
[52] U.S. Cl. ................................ 424/70.5; 424/70.2
[58] Field of Search ............... 424/70.5, 70.2, 424/70.51

[56] References Cited

U.S. PATENT DOCUMENTS

| | | | |
|---|---|---|---|
| 2,719,813 | 10/1955 | Haekle | 167/87.1 |
| 2,719,814 | 10/1955 | Haelek | 167/87.1 |
| 3,840,656 | 10/1974 | Kalupissis | 424/47 |
| 4,158,704 | 6/1979 | Baer | 424/72 |
| 4,935,230 | 6/1990 | Naito | 424/70 |
| 5,068,102 | 11/1991 | Tennigkeit | 424/72 |
| 5,350,572 | 9/1994 | Savaides | 424/71 |
| 5,378,454 | 1/1995 | Burmeister | 424/70.5 |

OTHER PUBLICATIONS

Zviak, *The Science of Hair Care*, 1986 pp. 190–192, 197, 198.

*Primary Examiner*—Sally Gardner-Lane
*Attorney, Agent, or Firm*—Londa and Traub LLP

[57] ABSTRACT

The object of the invention is a composition for permanent waving of human hair comprising, as sole or main reducing agent one or several polyglycol monothioglycollates or lactates of the general formula

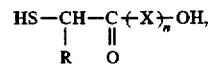

wherein R denotes a hydrogen atom or a methyl group, X represents an ethoxy or propoxy group, and n is a number from 2 to 5. These compositions have a low characteristic smell, good waving properties, and an extremely low skin sensitizing potential.

10 Claims, No Drawings

COMPOSITION FOR PERMANENT WAVING OF HUMAN HAIR

This invention refers to a composition for permanent waving of human hair with good waving properties having a low characteristic smell and in particular an extremely low skin sensitizing potential.

It is well-known that permanent waving is usually performed in two steps:

The reductive splitting of the cystine disulfide bonds of the hair by the reaction of a reducing agent and the subsequent neutralizing or fixing process by the application of an oxidizing agent, whereby the cystine disulfide bonds are re-established.

The reducing agent mainly used is still thioglycolic acid, particularly its ammonium salt, although numerous other thio compounds have been suggested for this purpose, e.g. thiolactic acid, 3-mercaptopropionic acid, thiotartaric acid, thiomalic acid, dimercaptoadipinic acid, cysteine, N-acetyl cysteine, homocysteine and other mercaptocarboxylates, cysteamine, N-acyl cysteamine and other cysteamine derivatives, 2-mercaptoethanol, thioglycerol, 3-alkoxy-1-mercapto-propanols and other mercapto-alcohols, methyl thioglycollate, ethyl thioglycollate, glycol monothioglycollates, 1,2-propyleneglycol monothioglycollate, 1,3-propyleneglycol monothioglycollate, glycerol monothioglycollate, glycol monothiolactate, glycerol monothiolactate, glycerol mono-3-mercaptopropionate, cysteine methyl ester, cysteine ethyl ester, homocysteine methyl ester, homocysteine ethyl ester and other mercaptocarboxylates, thioglycolic amide, N-hydroxyethyl thioglycolic amide, 3-mercaptopropionic amide, N-hydroxyethyl 3-mercaptopropionic amide, cysteine amide, and other mercaptocarboxylic acid amides which, however, have not been successful in practice.

The thioglycollate compositions are usually applied at a pH-value between 8 and 10, particularly 8.5 to 9.5, which may lead to hair damage if applied repeatedly within short intervals.

It has already been tried to overcome these disadvantages by the creation of so-called "acidic permanent waving compositions" having a pH at use of about 6.8 to 7.8, i.e. close to neutral. The reducing agent mainly used in these compositions is thioglycolic acid monoglycerol ester. However, this substance is supposed to have an irritating and especially sensitizing effect on some users so that this solution of the problem is not optimal.

It has now been found that these problems may be overcome while obtaining permanent waving compositions acting at a pH-value where no hair damage occurs but which still have a good waving effect, if a composition is used comprising as reducing agent a compound of the formula

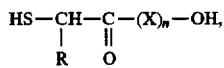

wherein R denotes hydrogen or a methyl group, X stands for a ethoxy or propoxy group, and n is a number from 2 to 5.

Particularly preferred for this purpose are diethyleneglycol monothioglycollate, triethyleneglycol monothioglycollate, tetraethyleneglycol monothioglycollate, diethyleneglycol monothiolactate, triethyleneglycol monothiolactate, tetraethyleneglycol monothiolactate, dipropyleneglycol monothioglycollate, dipropyleneglycol monothiolactate, as well as polypropyleneglycol(3)- and polypropyleneglycol(4) monothioglycollate and -monothiolactate.

Mixtures of the above cited polyethylene and polypropyleneglycol thioesters and particularly isomer mixtures thereof may, of course, also be used.

German Patent Application No. 40 03 234 already discloses permanent waving compositions comprising as active agents, i.e. reducing agents, monothiolactic acid glycerol ester. It also contains a survey of the state of the art to which reference is expressly made.

Moreover, German Patent No.39 20 984 describes permanent waving compositions comprising mixtures of glycerol monothioglycollate and 2- or 3-mercaptopropionic acid monoglycerol ester.

All these compositions and mixtures, however, are not optimal in respect of their waving effect and may cause skin sensitization of the persons treated thereby and in particular of the hairdressers' hands if applied repeatedly.

German Patent Application No.22 55 800 already describes permanent waving compositions containing as active agents, i.e. reducing agents, esters from polyvalent alcohols and low mercapto carboxylic acids. As such, 1,2-propyleneglycol monothioglycolic acid ester is also mentioned.

This course is continued by Patent No. WO-A 93/01791 describing an azeotropic mixture of two isomers of 1,2-propanediol monothioglycollate and their use as reducing agents in permanent waving compositions.

According to the invention, it has been found that a permanent waving composition comprising monothioglycolic acid or monothiolactic acid esters according to the above general formula, has at least the same permanent waving properties as known thioglycolic acid esters with the usual polyalcohols, e.g. ethyleneglycol monothioglycollate, 1,2-propyleneglycol monothioglycollate, 1,3-propyleneglycol monothioglycollate, and glycerol monothioglycollate, causes no sensitizing effect, has less smell than the esters mentioned before, and, therefore, has superior qualities compared with conventional thioglycolic acid esters.

From these esters, homogeneous aqueous permanent waving compositions may be prepared.

The production of the polyethylene- and polypropyleneglycol thioglycollate or thiolactic acid monoesters is effected according to the following reaction pattern:

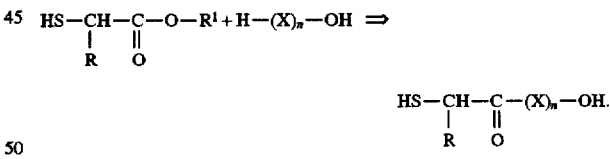

(In these formulae, R denotes a hydrogen atom or an methyl group, and $R^1$ is a hydrogen atom or a low alkyl group bearing 1 to 4 carbon atoms; X and n have the same valency as previously mentioned).

Thus, thioglycolic acid and thiolactic acid, resp., or alkyl thioglycollates and alkyl thiolactates, resp., are made to react with the corresponding polyglycols.

This reaction may be performed without or with a solvent such as toluene or 1,2-dichloroethane; the reaction may be effected without or with a catalyst such as sulfuric acid, benzene sulfonic acid or p-toluene sulfonic acid. The preferred reaction temperature is about 50° C. to 200° C., and, particularly preferred, about 80° C. to 180° C. The molar ratio of polyglycol to thioglycolic acid and thiolactic acid, resp., or to alkyl thioglycollate and thiolactate, resp., is preferably between 1 and 20, particularly between 1.5 and 3.

To improve the reaction, the water that develops during the reaction is preferably removed. After completed reaction, the reaction products are easily purified by column chromatography. To improve compatibility, the quantity of the diester co-produced so far should not exceed 10% by wt., preferably 5% by wt.

In addition to thioglycolic ester reducing agents according to the invention, the permanent waving composition may comprise further known reducing agents, e.g., one or more compounds selected from the group of thioglycolic acid, thiolactic acid, thiomalic acid, thiotartaric acid, dimercaptoadipinic acid, cysteine, N-acetyl cysteine, cysteine amide, homocysteine, cysteamine, N-acetyl cysteamine, mercaptoethanol, thioglycerol, ethyleneglycol monothioglycollate, 1,2-propyleneglycol monothioglycollate, 1,3-propyleneglycol monothioglycollate, glycol monothiolactate, glycerol monothiolactate and the salts thereof, provided that they do not have a negative influence on the effect of the reducing agent according to the invention.

The total proportion of polyethylene or polypropyleneglycol dithioglycollate or dithiolactate shall not exceed about 10% by wt., calculated to the mixture of monothioglycollate or monothiolactate, it shall preferably be less than 5% by wt., particularly only 2% by wt. or most preferably 1% by wt.

The preferred proportion of polyethylene or polypropyleneglycol monothioglycollate or -monothiolactate in the permanent waving compositions according to the invention is from about 5% to about 35% by wt., calculated to the total reducing composition (i.e. excluding the fixing or neutralizing composition), particularly about between 10% to 15% and about 25% by wt.

If other reducing agents are present in admixture with the polyglycol thioesters in permanent waving compositions according to the invention, their proportion is preferably below 50%, particularly below 25%, calculated to the total percentage of reducing agents.

In any case, however, the polyglycol monothioester represents the main proportion of the total reducing agent, preferably between 65% and 100% thereof.

If the polyglycol thioester is used in admixture with other reducing agents, its proportion of the total reducing agent must be reduced accordingly; the quantity depends on the type and proportion of the other reducing agent(s).

The total reducing agent content is normally from 2.5% to about 15% by wt., calculated to free thioglycolic acid as reference substance.

If required, the reducing permanent waving compositions may contain alkalizing agents. Their amount depends on the character of the reducing ingredient and the desired pH-value of the composition. The reducing agent composition preferably comprises about 0.1% to about 5%, particularly between about 0.5% and about 2.5% by wt. thereof.

Within the scope of the invention, preferred alkalizing agents are ammonium carbamate, ammonia, and (or) ammonium (bi)carbonate. The preferred pH-value is in the range between about 6 and about 9.5, preferably about 7 to 8.5.

The permanent waving compositions according to the invention preferably also contain surfactants. Their proportion is about 0.1% to about 10%, particularly about 1% to about 5% by wt. of the reducing agent composition.

The surfactants used in both reducing agent compositions and neutralizing compositions are preferably the well-known anionic compounds which may optionally also be used in combination with nonionic surfactants.

Suitable anionic surfactants are the well-known alkyl ether sulfates and carboxylic acids, preferably in the form of their alkali salts, and protein fatty acid condensates.

Suitable nonionic surfactants are particularly $C_8-C_{18}$-fatty alcohol polyglycol ethers, fatty acid polyglycol esters, fatty acid alkanolamides, amine oxides and, preferably, $C_8-C_{18}$-alkyl polyglucosides.

Amphoteric surfactants may also be used, such as the well-known betaines and amido betaines and, especially in cationic neutralizing compositions, cation-active surfactants such as quaternary ammonium compounds.

Another desirable component of the reducing agent compositions according to the invention are $C_3-C_6$-alkanediols or ethers thereof, particularly mono-$C_1-C_3$-alkyl ethers.

Preferred substances in this context are 1,2- and 1,3-propanediol, 1-methoxypropanol(-2), 1-ethoxypropanol(-2), 1,3- and 1,4-butanediol, diethyleneglycol, and the monomethyl and monoethyl ethers thereof as well as dipropyleneglycol and the monomethyl and monoethyl ethers thereof.

The percentage of these diols is preferably between 0.5% and 30%, more preferably from about 1% to about 15%, particularly about 5% to about 10% by wt. of the reducing agent composition.

In addition to $C_3-C_6$-alkanediols or the ethers thereof, monoalcohols may also be used, such as ethanol, propanol-1, propanol-2, as well as polyalcohols, such as glycerol and hexanetriol, ethyl carbitol, benzyl alcohol, benzyl oxyethanol, and propylene carbonate (4-methyl 1,3-dioxolane-2-on), N-alkyl pyrrolidone and urea.

The compositions according to the invention may, of course, comprise any ingredients common in permanent waving compositions; they may be formulated as (aqueous) solutions, emulsions, creams, foams, etc.

To avoid repetition, reference is made to the state of the art, e.g., as described in "Ullmann's Encyclopedia of Chemical Chemistry", Vol. A12 (1986), pp. 588 to 591, and particularly the monography of K.Schrader, "Grundlagen und Rezepturen der Kosmetika", 2nd Ed. (1989, Hüthig-Verlag, Heidelberg), pp. 823 to 840, as well as the survey of D.Hollenberg et al. in "Seifen-Öle-Fette-Wachse" 117 (1991), pp.81 to 87.

The compositions and ingredients disclosed therein are expressly included and may also be used within the scope of the present invention.

Optionally a pre-treatment may be applied before the application of the reducing agent as described, e.g., in German Patent Application No.37 40 926. After that, the hair is wound on curlers, then the reducing agent is applied. After about 15 to 30 minutes processing time and rinsing with water, the hair is neutralized with one of the usual peroxide or bromate compositions which are well-known from the state of the art.

Of course, an intermediate treatment known per se may also be applied between the reducing and the neutralizing steps.

The following Examples illustrate the invention in detail.

PRODUCTION EXAMPLE 1

Synthesis of diethyleneglycol monothioglycollate

In a reaction vessel, a mixture of 86.4 g (0.841 moles) diethyleneglycol and 50.0 g (0.534 moles) thioglycolic acid were stirred at 170° C. to 180° C. under nitrogen atmosphere for three hours. After completed reaction, the liquid was cooled down, and a mixture consisting of 49% diethyleneglycol monothioglycollate, 19% diethyleneglycol dithioglycollate, and 32% diethyleneglycol was obtained. The yield of diethyleneglycol monothioglycollate was 64%.

The reaction product was further purified as follows:

The mixture obtained was distilled under vacuum (0.1 to 0.3 mmHg); after removal of 50.4 g of the initial product, 46.5 g of the main product were obtained at 108° C. to 110° C., having a purity of >96%. The mixture contained 96% diethyleneglycol monothioglycollate and 4% diethyleneglycol dithioglycollate. The total yield was 47%.

PRODUCTION EXAMPLE 2

In a reaction vessel, 150.0 g (1.41 moles) diethyleneglycol, 50.0 g (0.471 moles) methyl thioglycollate, and 0.5 g sulfuric acid were stirred under nitrogen atmosphere at 90° C. for four hours. After completed reaction, the mixture was purified twice by silica column chromatography (1 kg silica [Merck], mesh 230 to 400, elution solvent: Chloroform). The solvent was evaporated from the eluate; after drying and distilling at 97° to 100° C. and 0.2 mmHg, 34.7 g (0.22 moles) of diethyleneglycol monothioglycollate were obtained. This was purified once more by silica column chromatography (1 kg silica 60 [Merck]; mesh 230; eluent: Chloroform/methanol in a ratio of 50:1 to 20:1). The solvent was evaporated from diethyleneglycol monothioglycollate under vacuum, and the remainder was dried, yielding 31.3 g (0.17 moles, corresponding to 37% yield) of diethyleneglycol monothioglycollate having a purity of >99%.

$^1$H-NMR-spectrum (200 MHz, DMSO-$d_6$) δ/ppm: 2.93 (1H, brt H$^A$), 3.36 (2H, d, H$^B$), 3.46 (3H, t, H$^D$, H$^E$), 3.62 (2H, t, H$^F$), 4.18 (2H, t, H$^C$), 4.60 (1H, br, H$^G$).

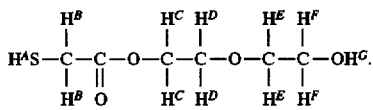

PRODUCTION EXAMPLE 3

In a reaction vessel, 229.0 g (1.53 moles) triethyleneglycol, 50.0 g (0.54 moles) thioglycolic acid and 0.5 g sulfuric acid were stirred at 100° C. under nitrogen atmosphere for 3.5 hours. After the reaction, the mixture was purified with silica column chromatography (1.2 kg silica 60 [Merck] and 230 to 400 mesh; eluate: Chloroform and chloroform/methanol in a ratio of 20:1). The solvent was evaporated under vacuum and the remainder was dried; the yield was 44.5 g (0.20 moles, corresponding to 37%) of triethyleneglycol monothioglycollate having a purity >99%.

$^1$H-NMR spectrum (200 MHz, DMSO-$d_6$) δ/ppm: 2.94 (1H, brt, H$^A$), 3.35 (2H, d, H$^B$) 3.41-3.52 (8H, m, H$^D$-H$^G$), 3.61 (2H, t, H$^H$), 4.17 (2H; t; H$^C$), 4.58 (1H, brs, H$^I$).

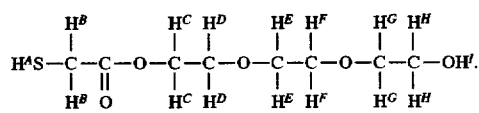

PRODUCTION EXAMPLE 4

In a reaction vessel, 273.0 g (1.41 moles) tetraethyleneglycol, 50.0 g (0.47 moles) methyl thioglycollate, and 0.5 g sulfuric acid were stirred at 110° C. under a nitrogen atmosphere for 3 hours. After the reaction, the mixture was purified twice with silica column chromatography (1–2 kg silica 60 [Merck], mesh 230–240; eluate: Chloroform and chloroform/methanol in a ratio of 50:1). The solvent was evaporated under vacuum from the eluate containing tetraethyleneglycol monothioglycollate, and the remainder was dried; the yield was 27.0 g (0.10 moles; corresponding to 21%) of tetraethyleneglycol monothioglycollate having a purity of >99%.

$^1$H-NMR spectrum (200 MHz; DMSO-$d_6$) δ/ppm: 2.96 (1H, brt, H$^A$), 3.35 (2H, d, H$^B$), 3.39–3.52 (12H, m, H$^D$-H$^I$), 3.61 (2H, t, H$^J$), 4.17 (2H, t, H$^C$), 4.58 (1H, brs, H$^K$).

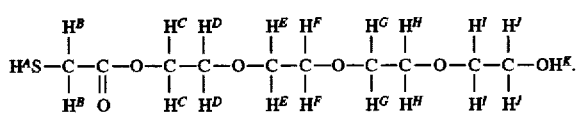

Stability tests

Reducing agent mixture:

N1: Mixture comprising 49% diethyleneglycol monothioglycollate, 19% diethyleneglycol dithiothioglycollate, and 32% diethyleneglycol.

N2: Mixture comprising 96% diethyleneglycol monothioglycollate and 4% diethyleneglycol dithioglycollate.

N3: Diethyleneglycol monothioglycollate (>99%)

N4: Triethyleneglycol monothioglycollate (>99%).

N5: Tetraethyleneglycol monothioglycollate (>99%)

N6: Mixture of 96% 1,2-propyleneglycol monothioglycollate and 4% 1,2-propyleneglycol dithioglycollate.

TABLE 1

|   | 1 | 2 | 3 | 4 | 5 | Comparison Example I. |
|---|---|---|---|---|---|---|
| N1 | 27.8 g | — | — | — | — | — |
| N2 | — | 20.8 g | — | — | — | — |
| N3 | — | — | 21.4 g | — | — | — |
| N4 | — | — | — | 26.3 g | — | — |
| N5 | — | — | — | — | 31.5 g | — |
| N6 | — | — | — | — | — | 17.4 g |
| NH$_4$HCO$_3$ | 0.87 g | 0.87 g | 0.87 g | 0.87 g | 0.87 g | 0.87 g |
| 28% NH$_4$OH | q.s. | q.s. | q.s. | q.s. | q.s. | q.s. |
| Water | @ 100 g | @ 100 g | @ 100 g | @ 100 g | @ 100 g | @ 100 g |
| pH-value | 7.2 | 7.2 | 7.2 | 7.2 | 7.2 | 7.2 |

The stability tests of compositions 1 to 5 and of Comparison Example I showed the following results:

Composition according to Example 1 (comprising reducing agent N1):

Becoming turbid immediately after mixing, separating into two layers 10 minutes later.

Composition according to Example 2 (comprising reducing agent N2):

The composition was a homogeneous and transparent solution.

Composition according to Example 3 (comprising reducing agent N3):

The composition was a homogeneous and transparent solution.

Composition according to Example 4 (comprising reducing agent N4):

The composition was a homogeneous and transparent solution.

Composition according to Example 5 (comprising reducing agent N5):

The composition was a homogeneous and transparent solution.

Composition according to Comparison Example I (comprising reducing agent N6):

Becoming turbid immediately after mixing, separating into two layers 10 minutes later.

Odor tests

Compositions according to Table 2 (each comprising equal molar quantities of the individual reducing ingredients) were prepared for odor evaluation.

TABLE 2

|  | Example 3 | Comparison Example I |
|---|---|---|
| N3 | 21.1 g | — |
| N6 | — | 17.6 g |
| NH$_4$HCO$_3$ | 0.87 g | 0.87 g |
| 28% NH$_4$OH | q.s. | q.s. |
| Water | @ 100 g | @ 100 g |
| pH-value | 7.2 | 7.2 |

Results of odor test:

Composition according to Example 3 (comprising reducing agent N3):

No intense characteristic smell.

Composition according to Comparison Example I (comprising reducing agent N6):

A strong characteristic smell was noted.

Evaluation of waving performance

The compositions according to Table 3 comprise equal molar quantities of the reducing agents.

Damaged European human hair was subjected to a permanent waving treatment wherein, in each case, the same permanent waving compositions were used (permanent waving treatment at room temperature for 10 minutes each; rinsing the hair with water at room temperature; thereafter 10 minutes treatment of the hair with a neutralizing agent at room temperature); then evaluation of waving performance of the individual compositions.

TABLE 3

| Examples | 2 | 3 | 4 | 5 | Comparison Example II. |
|---|---|---|---|---|---|
| N1 | — | — | — | — | — |
| N2 | 20.8 g | — | — | — | — |
| N3 | — | 21.1 g | — | — | — |
| N4 | — | — | 26.3 g | — | — |

TABLE 3-continued

| Examples | 2 | 3 | 4 | 5 | Comparison Example II. |
|---|---|---|---|---|---|
| N5 | — | — | — | 31.5 | — |
| N7 | — | — | — | — | 21.6 g |
| NH$_4$HCO$_3$ | 0.87 g | 0.87 g | 0.87 g | 0.87 g | 0.87 g |
| 28% NH$_4$OH | q.s. | q.s. | q.s. | q.s. | q.s. |
| Water | @ 100 g | @ 100 g | @ 100 g | @ 100 g | @ 100 g |
| pH-value | 7.2 | 7.2 | 7.2 | 7.2 | 8.5 |

| Neutralizing Composition | |
|---|---|
| 35% Hydrogen peroxide | 7.1 g |
| Phosphoric acid | q.s. |
| Water | @ 100 g |
| pH-value | 3.5 |

N7: 50% aqueous ammonium thioglycollate solution.

Evaluation of waving performance:

Composition according to Example 2 (reducing agent N2):

The hair showed a completely uniform permanent waving.

Composition according to Example 3 (reducing agent N3):

The hair showed a completely uniform permanent waving.

Composition according to Example 4 (reducing agent N4):

The hair showed a completely uniform permanent waving.

Composition according to Example 5 (reducing agent N5):

The hair showed a completely uniform permanent waving.

Composition according to Comparison Example II (reducing agent N7):

A considerably non-uniform permanent waving result was noted.

EXAMPLES 6 AND 7

The waving performance on damaged European human hair was, as described before, tested with the solutions listed in Table 4, and then fixed with the corresponding neutralizing compositions.

TABLE 4

| Examples | 6 | 7 |
|---|---|---|
| N2 | 17.3 g | — |
| N3 | — | 17.6 g |
| N7 | 2.7 g | 2.7 g |
| NH$_4$HCO$_3$ | 0.87 g | 0.87 |
| 28% NH$_4$OH | q.s. | q.s. |
| Water | @ 100 g | @ 100 g |
| pH-value | 7.2 | 7.2 |

Evaluation of the permanent waving performance:

The hair had a completely uniform permanent waving; no excessive perming was noted.

Sensitivity test

The sensitizing potential of diethyleneglycol monothioglycollate (N2) was tested vs. glycerol monothioglycollate (GMTG) in the well-known Guinea Pig Maximization Test according to Magnusson and Kligman.

Results

Reducing agent N2:

In a group of 10 sensitized animals no positive reaction occurred.

Glycerol monothioglycollate:

In a group of 10 sensitized animals a positive reaction was noted in 7 cases.

These tests prove that effective permanent waving compositions without sensitizing effect may be obtained by using polyglycol monothioglycollates according to the invention as reducing compounds.

The following examples describe two optimally composed permanent waving preparations comprising polyglycol thioesters according to the invention. Neutralization is performed with a usual neutralizing composition on the basis of hydrogen peroxide.

EXAMPLE 8

| Permanent wave for normal hair | | |
|---|---|---|
| Diethyleneglycol monothioglycollate (content of diethyleneglycol dithioglycollate <2% by wt.) | 21.00 | (% by wt.) |
| Chlorophyllin | 0.005 | |
| Ammonium carbamate | 0.75 | |
| Quaternary cationic polymer (Polyquaternium-2) | 0.50 | |
| Urea | 1.00 | |
| $C_9$-$C_{11}$-Alkyl polyglucoside (P.D.: ≈1.4) | 1.00 | |
| Castor oil polyglycol fatty acid ester | 0.50 | |
| Perfume | 0.40 | |
| Water | @ 100.00 | |
| Adjusted with ammonia to pH 7.0 | | |

EXAMPLE 9

| Permanent wave for porous hair | | |
|---|---|---|
| Diethyleneglycol monothioglycollate (diethyleneglycol dithioglycollate content about 1% by wt.) | 17.50 | (% by wt.) |
| Ammonium hydrogencarbonate | 0.90 | |
| Protein hydrolyzate (Nutrilan ®) | 0.30 | |
| Coconut amidopropyl betaine | 1.00 | |
| Lauryl alcohol ethoxylate (Laureth-23) | 1.00 | |
| Perfume oil | 0.40 | |
| Water | @ 100.00 | |
| Adjusted with ammonia to pH 7.1. | | |

PRODUCTION EXAMPLE 5

100 g (0.942 moles) diethyleneglycol and 50.0 g (0.471 moles) thiolactic acid were stirred in a reaction vessel at 150° to 160° C. under nitrogen atmosphere for 7 hours. After the reaction, the produced water was removed and the product was cooled down; the mixture contained 45% diethyleneglycol monothiolactate, 12% diethyleneglycol dithiolactate, and 43% diethyleneglycol.

The yield of diethyleneglycol monothiolactate was 70%.

The reaction mixture obtained was distilled under vacuum at 0.1 to 0.3 mmHg. After removal of 78.0 g pre-product, 46.0 g of the main product were distilled at 103° to 104° C. comprising 98% diethyleneglycol monothiolactate, 1% diethylenglycol dithiolactate, and 1% diethyleneglycol, corresponding to a yield of 56% diethyleneglycol monothiolactate.

PRODUCTION EXAMPLE 6

150.0 g (1.41 moles) diethyleneglycol, 50.0 g (0.471 moles) thiolactic acid and 0.5 g sulfuric acid were stirred in a reaction vessel at 120° C. under nitrogen atmosphere for 2 hours. After completed reaction, the mixture was purified twice by column chromatography on silica (1 kg Si 60 [Merck], 230–400 mesh; solvent for elution: Chloroform and chloroform/methanol (20:1)).

The solvent was evaporated under vacuum, the residue after drying was 37.5 g (0.19 moles) diethyleneglycol monothiolactate having a purity of >99%, corresponding to 41% yield.

$^1$H-NMR-Spectrum (DMSO-$d_6$) δ/ppm: 1.40 (3H, d, H$^C$, 3.23 (1H, d, H$^A$), 3.42–3.50 (5H, m, H$^B$, H$^E$ und H$^F$), 3.61 (2H, td, H$^G$), 4.17 (2H, t, H$^D$), 4.61 (1H, t, H$^H$).

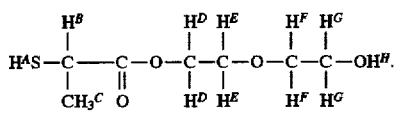

Odor test

The compositions listed in Table 5 were subjected to an odor test.

TABLE 5

| Examples | 10 | Comparison Example III. | Comparison Example IV. |
|---|---|---|---|
| N8 | 22.7 g | | |
| N9 | | 13.9 g | |
| N10 | | | 17.6 g |
| NH$_4$HCO$_3$ | 0.87 g | 0.87 g | 0.87 g |
| 28% NH$_4$OH | q.s. | q.s. | q.s. |
| Water | @ 100 g | @ 100 g | @ 100 g |
| pH | 7.2 | 7.2 | 7.2 |

N8: Diethyleneglycol monothiolactate (>99%).
N9: Ethyleneglycol monothioglycollate (>99%).
N10: Ethyleneglycol monothiolactate (>99%).

Evaluation of the odor test:

Composition according to Example 10 (containing N8): Only a weak characteristic smell was noted.

Composition according to Example 11 (containing N9): A strong characteristic smell was noted.

Composition according to Example 12 (containing N10): A strong characteristic smell was noted.

Evaluation of waving performance

The processes were conducted in accordance with the methods described above, using the reducing agent compositions as described in Table 6 and the corresponding neutralizer.

The following reducing agents were used:

N8: Diethyleneglycol monothiolactate (>99%).
N11: Mixture of 98% diethyleneglycol monothiolactate, 1% diethyleneglycol dithiolactate, and 1% diethyleneglycol.

N7: 50% aqueous ammonium thioglycollate solution.

TABLE 6

| Examples | 11 | 12 | Comparison Example VI. |
|---|---|---|---|
| N8 | 22.7 g | | |
| N11 | | 22.9 g | |
| N7 | | | 25.5 g |
| NH$_4$HCO$_3$ | 0.87 g | 0.87 g | 0.87 g |
| 28% NH$_4$OH | q.s. | q.s. | q.s. |
| Water | @ 199 g | @ 100 g | @ 100 g |
| pH-value | 7.2 | 7.2 | 7.2 |

Evaluation of waving performance

Composition according to Example 11 (containing N8):

The hair showed a complete and uniform permanent waving.

Composition according to Example 12 (containing N11):

The hair showed a complete and uniform permanent waving.

Composition according to Comparison Example VI (containing N7):

A considerably non-uniform permanent waving result was noted.

EXAMPLE 13

A reducing composition, comprising

| 18.6 g | Diethyleneglycol monothiolactate |
| 2.7 g | Ammonium thioglycollate, 50% |
| 0.87 g | Ammonium hydrogencarbonate, | filled up with water to 100 g, and adjusted with NH$_4$OH to a pH of 7.2, was, as decribed above, applied onto human hair, rinsed and neutralized.

The resulting permanent wave was uniform and complete.

PRODUCTION EXAMPLE 7

218.64 g (1.63 moles) dipropyleneglycol (containing isomers), 50.0 g (0.54 moles) thioglycolic acid, and 0.5 g sulfuric acid were stirred in a reactor at about 100° C. under nitrogen atmosphere for two hours.

Thereafter the reaction mixture was purified twice by column chromatography (2 kg Si 60 [Merck], 230–400 mesh, eluate: Chloroform or a mixture of chloroform/methanol, ratio 50:1). The solvent was evaporated under vacuum, and the residue was dried.

The result was 40.1 g (0.19 moles) of dipropyleneglycol monothioglycollate having 99% purity, corresponding to a yield of 36%.

The NMR spectrum showed a mixture of four isomers:

$^1$H-NMR spectrum (200 MHz, DMSO-d$_6$), δ-ppm: 1.01–1.02, 1.02, 1.08, 1.09, 1.16 (6H, d, hydrogen atoms of methyl groups of H$^{E1}$–H$^{E4}$, H$^{H1}$–H$^{H4}$), 2.91, 2.94 (1H, t, hydrogen atoms of mercapto groups of H$^{A1}$–H$^{H4}$), 4.45–4.60 (1H, br, hydrogen atoms of hydroxy groups of H$^{I1}$–H$^{I4}$), 3.979–4.03 (d, hydrogen atoms of methylene groups of H$^{C1}$–H$^{C3}$), 4.86–5.00 (m, hydrogen atoms of methine groups of H$^{D2}$ and H$^{D4}$), (8H) 3.15–3.55, 3.63–3.80 (m, other methylene or methine hydrogen atoms).

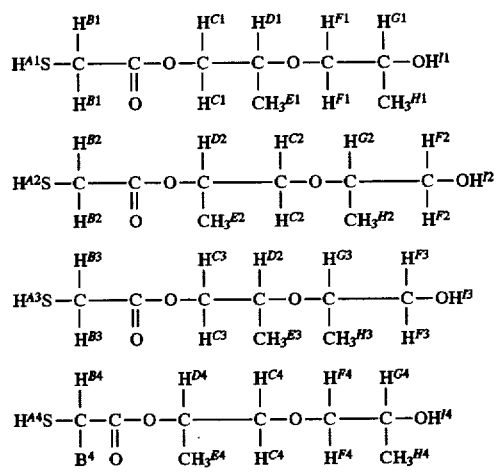

The dipropyleneglycol monothioglycollate obtained according to production Example 7, too, had only a weak characteristic smell and showed a waving performance comparable to diethyleneglycol monothioglycollate (cf. pp. 26/27)

The following Examples 14 and 15 present optimally formulated reducing agent compositions comprising diethyleneglycol monothiolactate and dipropyleneglycol monothioglycollate.

EXAMPLE 14

| Permanent waving composition for normal hair | | |
|---|---|---|
| Diethyleneglycol monothiolactate (<1% diethyleneglycol dithiolactate) | 22.50 | (% by wt.) |
| Chlorophyll | 0.005 | |
| Ammonium carbonate | 0.75 | |
| Polyquaternium-2 (Cationic polymer) | 0.50 | |
| Urea | 1.00 | |
| Coconut amidopropyl betaine | 1.00 | |
| Protein hydrolyzate (Nutrilan ®) | 0.50 | |
| Castor oil polyglycol fatty acid ester | 0.80 | |
| Perfume | 0.40 | |
| Water | @ 100.00 | |
| Adjusted to pH 7.2 with ammonia. | | |

EXAMPLE 15

| Permanent waving composition for normal hair | | |
|---|---|---|
| Dipropyleneglycol monothioglycollate (corresponding to Production Example 7) | 22.00 | (% by wt.) |
| 1,2-Propanediol | 40.00 | |
| Ammonium carbonate | 0.75 | |
| Urea | 1.00 | |
| Sodium alkylether sulfate/ protein fatty acid condensate (Olamine ® K) | 1.00 | |
| Castor oil polyglycol fatty acid ester | 0.80 | |
| Perfume | 0.40 | |
| Water | @ 100.00 | |
| Adjusted to pH 7.4 with ammonia. | | |

We claim:

1. Composition for permanent waving of human hair comprising from about 5% to about 30% by weight of one or more reducing agents of the general formula

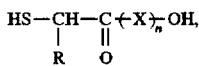

wherein R denotes hydrogen or a methyl group, X is an ethoxy or propoxy group, and n is a number from 2 to 5.

2. Composition according to claim 1, comprising, as reducing agent, diethyleneglycol monothioglycollate alone or in admixture with other reducing agents.

3. Composition according to claim 1, comprising, as reducing agent, diethyleneglycol monothiolactate alone or in admixture with other reducing agents.

4. Composition according to claim 1, comprising, as a reducing agent, triethyleneglycol monothioglycollate alone or in admixture with other reducing agents.

5. Composition according to claim 1, comprising, as reducing agent, dipropyleneglycol monothioglycollate alone or in admixture with other reducing agents.

6. Composition according to claim 1, comprising, as reducing agent, not more than 10% by wt., calculated to the reducing agent, of polyglycol dithioglycollate or dithiolactate.

7. Composition according to claim 6, wherein the reducing agent comprises not more than 5% by wt., calculated to the reducing agent, of polyglycol dithioglycollate or dithiolactate.

8. Composition according to claim 7, wherein the reducing agent comprises not more than 2% by wt., calculated to the reducing agent, of polyglycol dithioglycollate or dithiolactate.

9. Composition according to claim 1, comprising one or more additional reducing agents selected from the group consisting of thioglycolic acid, thiolactic acid, thiomalic acid, thiotartaric acid, dimercapto adipic acid, cysteine, N-acetyl cysteine, cysteine amide, homocysteine, cysteamine, N-acetyl cysteamine, mercaptoethanol, thioglycerol, ethanediol monothioglycollate, 1,2-propanediol monothioglycollate, 1,3-propanediol monothioglycollate, ethanediol monothiolactate, and 1,2-propanediol monothiolactate, and 1,3-propanediol monothiolactate.

10. Composition according to claim 1, comprising one or more compounds selected from the group consisting of ethanol, propanol-1, propanol-2, 1,2-propanediol, 1,3-butanediol, hexanetriol, glycerol, ethyl carbitol, benzyl alcohol, benzyl oxyethanol, urea, and 2-methyl pyrrolidone.

* * * * *